US011236296B2

(12) United States Patent
Viellerobe et al.

(10) Patent No.: US 11,236,296 B2
(45) Date of Patent: Feb. 1, 2022

(54) APPARATUS FOR THE TRANSFER OF BIO-INK

(71) Applicant: Poietis, Pessac (FR)

(72) Inventors: Bertrand Viellerobe, Merignac (FR); Romain Vaucelle, Bordeaux (FR); Fabien Guillemot, Preignac (FR)

(73) Assignee: Poietis, Pessac (FR)

( * ) Notice: Subject to any disclaimer, the term of this patent is extended or adjusted under 35 U.S.C. 154(b) by 225 days.

(21) Appl. No.: 16/494,649

(22) PCT Filed: Mar. 8, 2018

(86) PCT No.: PCT/FR2018/050533
§ 371 (c)(1),
(2) Date: Sep. 16, 2019

(87) PCT Pub. No.: WO2018/167400
PCT Pub. Date: Sep. 20, 2018

(65) Prior Publication Data
US 2020/0010787 A1   Jan. 9, 2020

(30) Foreign Application Priority Data

Mar. 15, 2017   (FR) ...................................... 1752129

(51) Int. Cl.
*C12M 3/00* (2006.01)
*B33Y 10/00* (2015.01)
(Continued)

(52) U.S. Cl.
CPC ............. *C12M 21/08* (2013.01); *B33Y 10/00* (2014.12); *B33Y 30/00* (2014.12); *C12M 31/00* (2013.01); *C12M 33/04* (2013.01); *B33Y 70/00* (2014.12)

(58) Field of Classification Search
CPC ..................................................... C12M 21/08
See application file for complete search history.

(56) References Cited

FOREIGN PATENT DOCUMENTS

| WO | 2016/097619 A1 | 6/2016 |
| WO | 2016/097620 A1 | 6/2016 |
| WO | 2017/011854 A1 | 1/2017 |

OTHER PUBLICATIONS

Guillemot et al., High-Throughput Laser Printing of Cells and Biomaterials for Tissue Engineering, Acta Biomater, vol. 6, No. 7, (Jul. 2010), pp. 2494-2500, (abstract only).
(Continued)

*Primary Examiner* — Larry W Thrower
(74) *Attorney, Agent, or Firm* — TraskBritt

(57) ABSTRACT

An apparatus for transferring bio-ink onto a target having a slide defining a receiving area of a film of fluid containing inhomogeneities, a laser source associated with controlled diversion means and an optical block for focusing in a plane of the fluid film in order to apply a local pulse, wherein the apparatus also comprises imaging means and means for analyzing images in order to recognize the geometric positions of the inhomogeneities in the film, and an observable feature of each of the inhomogeneities (size, shape factor, type of particles, age of the particle, density, type of biomaterial, molecule, etc.) recognized by the appropriate analysis means. The apparatus further comprises selection means for selecting at least one of the inhomogeneous areas, and means for controlling the diversion in order to direct the laser beam toward the position of the inhomogeneous area and trigger the firing of the laser.

30 Claims, 2 Drawing Sheets

(51) Int. Cl.
*B33Y 30/00* (2015.01)
*C12M 1/00* (2006.01)
*C12M 1/26* (2006.01)
*B33Y 70/00* (2020.01)

(56) References Cited

OTHER PUBLICATIONS

International Search Report for International Application No. PCT/FR2018/050533 dated Jun. 6, 2018, 2 pages.
International Written Opinion for International Application No. PCT/FR2018/050533 dated Jun. 6, 2018, 5 pages.
Santos et al., Real Time Imaging of Femtosecond Laser Induced Nanoneurosurgery dynamics in C. Elegans, Opt Express, vol. 18, No. 1, (Jan. 4, 2010), pp. 364-377, (abstract only).

APPARATUS FOR THE TRANSFER OF BIO-INK

CROSS-REFERENCE TO RELATED APPLICATIONS

This application is a national phase entry under 35 U.S.C. § 371 of International Patent Application PCT/FR2018/050533, filed Mar. 8, 2018, designating the United States of America and published as International Patent Publication WO 2018/167400 A1 on Sep. 20, 2018, which claims the benefit under Article 8 of the Patent Cooperation Treaty to French Patent Application Serial No. 1752129, filed Mar. 15, 2017.

TECHNICAL FIELD

The present disclosure concerns the field of laser bio-printing by a computer-assisted transfer process for modelling and assembling living and optionally non-living materials with a prescribed 2D or 3D organization in order to produce bioengineered structures for use in regenerative medicine, pharmacology and cell biology studies.

BACKGROUND

Laser-assisted bio-printing makes it possible to organize with high precision the individual elements of the tissue during its manufacture via the layer-by-layer deposition of cells and biomaterials. It allows to reproduce 3D tissue with a specific geometry. The "bottom-up" approach, based on assembling an object brick by brick and then layer by layer, is compatible with an automation of the tissue manufacturing process and can operate in a sterile environment. In addition, automation could reduce costs, improve the quality and reproducibility of biological tissue manufacturing.

The present disclosure concerns more particularly a laser-assisted deposition solution based on the direct (absorption of laser radiation) and indirect (creation of a plasma and a cavitation bubble) action of a laser beam to direct the deposition of particles on a printing substrate with a micrometric resolution.

The article by F. Guillemot, A. Souquet, S. Catros, B. Guillotin, J. Lopez, M. Faucon, B. Pippenger, R. Bareille, M. Rémy, S. Bellance, P. Chabassier, J. C. Fricain, and J. Amédée, "High-throughput laser printing of cells and biomaterials for tissue engineering," Acta Biomater. 6, 2494-2500 (2010), describes an example of equipment to implement such a process.

Patent Application Publication No. WO2016097619 describes a method and equipment for printing with at least one ink, the method comprising a step of focusing a laser beam so as to generate a cavitation bubble in an ink film, a step of forming at least one ink droplet from a free surface of the ink film and a step of depositing the droplet onto a depositing surface of a receiving substrate. The laser beam is oriented in the direction opposite to the gravitational force, the free surface of the film being oriented upward toward the depositing surface placed over the ink film.

This configuration makes it possible, in particular, to obtain a substantially constant thickness E for the ink film, while limiting the occurrence of settling phenomena. It also enables the use of a wide range of inks, and the use of time-resolved imaging (TRI) by shadowgraph to study and control the formation of jets.

Another example of a real-time imaging technique applied to the monitoring of laser ablation of neurons is described in the publication "Real time imaging of femtosecond laser-induced nano-neurosurgery dynamics in C. elegans," OPTICS EXPRESS 364, Vol. 18, No. 1, 4 Jan. 2010. In this configuration, the field of view is very small and focused on the laser ablation zone where a number of complex photochemical and photo-biological phenomena are studied. This is a general example of imaging associated with a laser-matter interaction process for micro-machining.

In the field of bio-printing, bio-inks are so-called inhomogeneous media, i.e., they contain either suspended particles or different biochemical species in solution (growth factors, biological molecules, ions, etc.) or biomaterials (uniformly distributed in solution, or in gradients or co-linear fluxes if there are several), or a more or less complex mixture of these three main components, the latter being the most common. The complexity of these inks, in particular, their inhomogeneity, is not addressed at all in the prior art of forward bio-printing by laser.

In addition, the prior art has shown that the particle density of a bio-ink is highly random (colloidal fluid), thus leading to a transfer of a number of particles to a receiving substrate in a statistical way.

In such a context, the solutions of the prior art do not allow to select in the bio-ink film with a precise composition (biochemical or biomaterial particles or species), according to particular characteristics distinguishing it from other elements composing the bio-ink present in the film, to transfer to the receptor the right bio-ink composition corresponding to the predefined bio-printing plan.

In the solutions of the prior art, the laser interacts with an area of the film supposed to contain inhomogeneities to be transferred "blindly," the film containing a sufficient density of transferable particles, even close to saturation, to ensure the transfer of a sufficient number of particles.

The film is periodically recharged manually with a fluid containing new particles, in order to maintain a sufficient number of particles, allowing a blind transfer. It can be pointed out that such a problem is ultimately common to all bio-printing processes, particularly ink-jet and extrusion.

BRIEF SUMMARY

As an initial matter, "inhomogeneity" of the bio-ink film means that any area of the film has its own characteristics in terms of composition: either particles, bio-chemical species (growth factors, biological molecules, ions, etc.) or biomaterials. In general, the terms "inhomogeneous zone," "local variation in composition," "specific composition zone" are used as synonyms for the generic term "inhomogeneity.".

In order to address these disadvantages, the present disclosure concerns, in its most general sense, equipment for the transfer of a bio-ink to a target comprising:
 a transparent slide defining a reception area for a heterogeneous fluid film containing either a plurality of particles and/or a plurality of biochemical species and/or a plurality of biomaterials, or a plurality of particles and/or one or more biomaterial types and/or one or more bio-chemical species and/or one or more bio-chemical species types;
 a laser source associated with a controlled deflection means and an optical unit for focusing in a plane of the fluid film to apply a localized pulse, wherein the equipment further comprises means for imaging an imaging area having an imaging section at least 5 times larger than the nominal section of an inhomogeneity of the bio-ink film;

image analysis means to recognize the geometric positions of the inhomogeneities in the film, and an observable characteristic of each of the recognized inhomogeneities (size, shape factor, type of particles, particle age, density and type of biomaterial, molecules, . . . ) by means of characterization means (e.g., optical imaging, Raman spectroscopy or auto-fluorescence analysis) and by spatio-temporal analysis means (dynamics of the individual and/or group of inhomogeneities behavior, etc.); and means for selecting at least one of the inhomogeneities thus located and characterized, and for controlling the deflection means to direct the laser beam toward the position of the inhomogeneities and to trigger the laser pulse.

According to some of its variants:

the upper imaging field is 1×1 mm;

the imaging field is scalable by applying a ROI (region of interest);

the imaging area includes the area of interaction of the laser with the fluid film;

the imaging area is distinct from the laser's interaction area with the fluid film, for example, on 2 distinct focal planes or on two adjacent areas of the same focal plane;

the equipment includes a local computer performing image processing to characterize the inhomogeneities present in the imaging area;

the equipment includes means of communication with a remote computer performing image processing to characterize the inhomogeneities present in the imaging area;

the means of characterization include one or more of the following elements: a mono- or multi-chromatic optical imaging system, a Raman spectrometer, an infra-red spectrometer or a means of analysis of the endogenous auto-fluorescence of the particles and biomaterials;

the film contains living cells, prokaryotic or eukaryotic, suspended or aggregated;

the film contains one or more biomaterials that can potentially be mixed with cells of one or more types as well as with biochemical species such as growth factors or determined biomolecules. Such a configuration opens the way to the creation of very complex and heterogeneous inks that can be used as "unique" inks to produce certain tissues by simplifying the process and making it faster and less expensive. The complexity will then lie in the ability of the present disclosure to quickly address the location and characterization of multiple areas of particles, biomaterials and/or chemical species present in the fluid film to allow the controlled manufacture of complex and customizable tissues; and the system can also be advantageously combined with a continuous bio-ink recharging device to ensure high productivity while providing access to a wide range of inhomogeneities to be targeted to meet the predefined bio-printing plan.

The present disclosure also concerns a method for the transfer of a bio-ink comprising inhomogeneities to a target consisting in placing in a transfer equipment a transparent slide defining a reception area of a transparent fluid film containing a plurality of inhomogeneities (particles or biochemical or biomaterial species) and controlling the orientation and activation of a laser pulse emitted by a laser associated with a controlled deflection means, to cause an interaction of the laser beam with the film, characterized in that the method further comprises:

a) at least one imaging step of an area of the film with an imaging cross-section at least 5 times larger than the nominal cross-section of an inhomogeneity;

b) at least one image analysis step to recognize the geometric positions of the inhomogeneities and at least one observable characteristic of each of the recognized inhomogeneities (size, shape factor, particle type, particle age, type and density of biomaterial, molecule, . . . );

c) at least one step of selecting one of the inhomogeneities thus located and characterized; and d) at least one transfer step comprising a control of the deflection means for directing the laser beam to the position of the selected inhomogeneity and a control for triggering a laser pulse.

According to process variants:

it also includes an imaging, analysis and characterization step and a plurality of transfer steps each corresponding to at least one localized and characterized area to be transferred;

it includes alternating imaging, analysis and characterization steps on the one hand, and transfer steps on the other;

it includes a step of calculating an ordered sequence of fields to be transferred;

the imaging step involves processing the raw images to extract simplified patterns corresponding to the areas to be transferred;

the steps of position calculation and characterization of the areas to be transferred are performed simultaneously;

the steps of calculating the position and characterizing the areas to be transferred are performed by processing based on algorithms executed on parallel architecture processors;

it includes an additional step of comparing an image of the printed area after a transfer, and a map of theoretical implantations;

it includes an additional step of triggering a new transfer to correct the difference between the observed transfer and the theoretical implantation;

the film contains living cells;

the film contains one or more types of biochemical species;

the film contains one or more types of biomaterials;

the film contains different concentrations of the same biomaterial;

and the process may also include means for recharging the bio-ink film to continuously or discontinuously fill the laser pulse area. The inhomogeneities of the bio-ink are then necessarily in motion within the film, which implies the use of appropriate means of data acquisition and processing to quickly and reliably characterize the bio-ink. These means may include the use of imaging, spectroscopy, physico-chemical analysis, on-line measurement, etc.

For the purposes of the present disclosure, "inhomogeneity" means an area of interest of bio-ink of organic, mineral or living composition, in particular:

nanoscopic particles such as exosomes or other vesicles produced by cells or nanoparticles of biomaterials (hydroxyapatite) or nanocapsules of biomolecules (growth factors);

microscopic particles such as living cells (eukaryotic cells, stem cells, globules, . . . ), micro-particles of biomaterials, micro-capsules of biomolecules (growth factors); and mesoscopic particles such as spheroids made up of clusters of cells or biomaterials.

Preferably, in the context of bio-printing, particles are defined as objects with biological properties, such as living cells, exosomes or biomolecules.

However, this equipment and the corresponding process do not stop at this definition of the present disclosure. Indeed, particles can also be non-biological (i.e., inert) and composed, for example, of one or more biomaterials, their nature depending on the targeted application.

BRIEF DESCRIPTION OF THE DRAWINGS

Other characteristics and advantages will appear from the following description of the present disclosure, the description being given by way of example only, with reference to the appended drawings in which.

DETAILED DESCRIPTION

Figure 1:
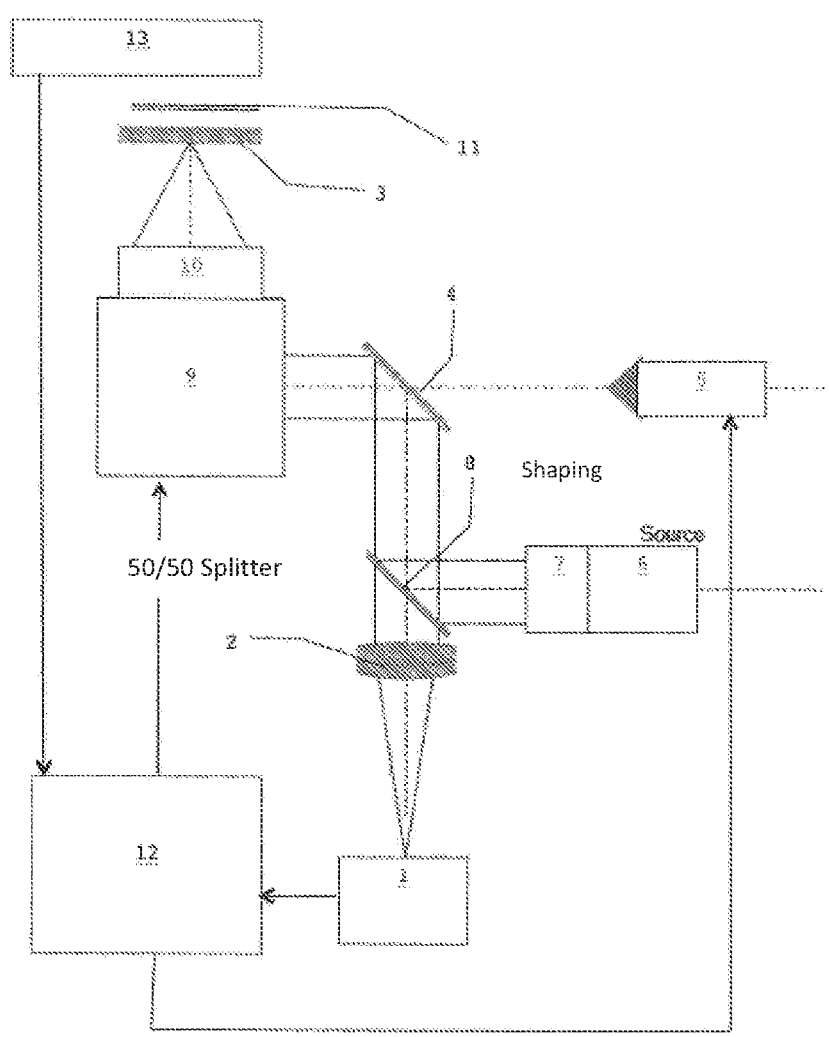
FIG. 1 is a schematic view of an equipment according to the present disclosure.

The present disclosure is part of the field of laser bio-printing (LAB), which aims to reconstruct human tissues in 3D. The LAB principle involves focusing a laser to create a plasma by absorption on a bio-ink film consisting of a solution of biomaterials, biochemical species and/or a cell suspension in a liquid medium. From this plasma, a cavitation bubble is generated in the bio-ink. This bubble, through its hydrodynamic movement, deforms the free surface of the bio-ink to the point of creating a stream of matter. The characteristics of this stream depend on a large number of physical parameters. It is through this stream (which contains a small number of cells, biomaterials or chemical species) that the transfer of material to the receiving substrate takes place in a controlled manner.

In this context, it is necessary to print the constituents of biological tissues according to specific patterns/locations in order to obtain either 2D/3D objects that will have properties (shapes and functions) as close as possible to native living tissues, or chimeras allowing to render more complex, test, and/or simplify biological contexts to improve the understanding of tissue morphogenesis or biological response mechanisms to external agents (active agents).

Thus, the printing of biomaterials carried out in conjunction with that of cells must also follow very specific printing schemes in order to provide a viable environment to the printed cells in order to achieve the requested item. In summary, controlling the quantity and position of cells, biomaterials, and/or biochemical species printed on the receiving substrate is essential to achieve the necessary and expected quality of bio-printed items.

The purpose of the present disclosure is to set up a measuring device allowing identification and/or mapping of areas of specific composition in an inhomogeneous bio-ink before printing and thus trigger the laser to aim specifically at a desired composition area according to the area to be printed (on the "receiver") and the pattern designed during the CAD of the target item.

To this end, the invention comprises: i) carrying out a 2D characterization of the donor, ii) detecting inhomogeneities by ad-hoc digital processing, iii) automatically mapping the positions of specific composition areas, and iv) matching the laser shooting pattern (printing trajectory) with the mapping of areas of specific donor composition.

In the context of bio-printing, particularly when developing new models, markers can be used temporarily to tag cells by external agents (immuno-marking, fluorescence, etc.) to assist in the characterization of printed items. On the other hand, when producing models for in vitro or in vivo applications, the cells must remain fully preserved from any exogenous disturbances because they constitute the building blocks of the target tissue. Therefore, they cannot be marked by external agents in these cases. Thus, the detection of cells will be relatively complicated within culture media because their refractive index is quite close to that of water, the main component of these media. Cellular imaging therefore already presents an important problem to be addressed.

In addition, the filling dynamics of the printing head or the natural movement of the suspended cells have a direct impact on the position of the cells over time. This implies detecting their position repeatedly and at high frequency if the laser printing path is to be always in line with the mapping of their location. This has a direct consequence on the detection and mapping means which must operate at high speed (both for the hardware part allowing data acquisition and for the software part allowing data processing).

The problem posed, which the present disclosure aims to solve, is therefore manifold and includes: to detect local variations in the composition of bio-inks (inhomogeneities) that are difficult to visualize (imaging means+image processing), to map inhomogeneities (image processing allowing both their number and position in the donor to be given), and to perform laser shots in correspondence with the mapping (adaptation of the printing trajectory in real time).

According to a variant, the present disclosure also aims to cover very interesting cases of cell sorting:

being able to distinguish between living and dead cells in order to print only living cells;

being able to dissociate two cell types that would have been mixed (voluntarily by co-culture or not) in the same ink;

being able to distinguish between cells of the same type but with a high degree of disparity (stem cells, different levels of differentiation/maturity);

being able to distinguish between areas of concentrations of the same biomaterial that would be present in the observation area and produced voluntarily or not;

being able to distinguish between different biomaterials that would have been mixed in the same bio-ink.

At the performance level, the "Target-Shoot" function, object of this invention, may allow:

the streamlining of the printing process (ratio of the number of printed cells to the number of cells present in the bio-ink), otherwise known as "Printing Yield." This minimizes the number of cells not used during the process;

the optimizing of the process by choosing laser shooting zones based on the number of cells spatially present (without the need to use multiple laser shots to print the same area). This means optimizing the printing path to minimize the number of laser shots and thus minimize cellular stress;

speed up the process (if necessary) thanks to the efficiency of laser firing, otherwise known as "Printing Rate";

make the process compatible with a continuous recharging cartridge since the "Target-Shoot" method must allow at any time to measure the cell displacements in the bio-ink where the flow will be relatively high.

The stakes are also:
- to allow printing cells in small or rare quantities thanks to the mastery of the "Printing Yield." This is an extremely important point in relation to certain pharmaceutical, cosmetic or clinical applications where the number of available cells is very low.
- to allow for a advanced customization of tissue models by the controlled choice of laser firing areas according to the number of cells spatially present. Thus, the response to requests for the development of custom-made tissues from laboratories or manufacturers will be possible with a very wide range of markets and applications, made possible by the high resolution and high precision of the laser process assisted by the Target-Shot method.
- to allow industrialization of the process and the increase in its productivity thanks to the acceleration of the process ("Printing Rate") by the systematic efficiency of laser shots ensured by the Target-Shoot function.
- to make the use of the technology much easier because the handling of bio-inks will be optimized and automated with the continuous recharging cartridge.
- to control the number of particles transferred at any time during the bio-printing process (laser pre-print/laser post-print comparison) to ensure a good match between the printed pattern and the CAD-designed pattern.
- reduce the cost of bio-printing devices by integrating a single cartridge (or a reduced number of cartridges) into which the different tissue components that would be sorted at the time of transfer would be placed. Potentially, the cost reduction could even pave the way for the definition of a single-use cartridge that would be of great benefit for the use of bio-printing in the clinical field.

In accordance with the present disclosure, an apparatus includes a camera (1) comprising a high-definition sensor, for example, of 18 megapixels. For example, the camera (1) is a sensor marketed under the trade name "USB 3 uEye CP" by the IDS company of Obersulm, Germany.

This camera (1) is associated with a second image-combining optical unit (2) acting as a field lens and thus ensuring the combining of the image between the focal plane of the film (3) and the plane of the camera (1).

The film (3) is placed in front of a target (11) to which the cells or particles are transferred when a laser pulse is triggered.

For example, the second image-combining optical unit (2) consists of a lens, preferably telecentric, comprising at least two lenses optimized in the visible range.

The optical path is reflected by a high-pass dichroic mirror (4), transmitting infra-red (corresponding to the emission wavelength of the laser (5)) and reflecting wavelengths in the visible range.

The equipment also includes a light source (6) emitting in the visible range associated with a shaping optics (7) whose function is to collimate the light source (6) if necessary, for example, when the source is divergent from the emitted beam. This light source can be a single LED source, a component consisting of an array of LEDs, or a white light source such as incandescent lamps, halogen lamps, super-continuum lasers, etc. The light source can also consist of a narrow spectrum source (either by the very nature of the technology used or by the use of optical filters) that emits in the wavelengths that allow the fluorescence excitation of markers or particles.

A separator slide (8) is used to superimpose the lighting optical path and the observation optical path.

At the exit of the dichroic mirror (4), the two beams heading toward the scanner (lighting and laser) are co-linear with each other and are in fact also co-linear with the imaging beam returning from the film. Thus, the three beams are co-linear between the dichroic mirror (4) and the ink film (3).

They are deflected by a scanner (9) ensuring an orientation that is controlled by an external computer.

The scanner (9) provides an angular orientation of the three co-linear beams mentioned above, along two perpendicular axes, two of which beams are scanned on the donor containing the bio-ink and the last being "deflected" to a collimated imaging beam toward the imaging system. The scanner (9) includes, for example, two mirrors driven by an electromagnetic actuator, for example, one marketed by SCANLAB Company of Puchheim, Germany, under the trade name "SCANcube 14.".

The three observation, lighting and laser beams are thus co-linear and oriented in the same direction as the aperture of the scanner (9). Thus, the observation direction and the lighting direction follow the orientation of the laser beam.

The function of the optical unit (10) is to:
a) transform the angular orientation into a lateral positioning/displacement along two axes X,Y in the plane of the film (3);
b) focus the laser beam and the lighting beam in the same plane of the film (3); and
c) collect the light in the visible domain reflected by the film (3), to construct the observation image of the camera (1).

The optical unit (10) comprises of a set of lenses forming a telecentric lens with the following characteristics:

In the infra-red spectrum, the lens surfaces are treated with anti-reflective coatings to support high laser energies. This prevents the deterioration over time of the first optical unit (10), the design of which is calculated to prevent the creation of laser "hot spots" within the first optical unit (10).

The dichroic mirror (4) prevents the return of laser infra-red radiation to the camera (1) when a pulse is triggered. Optionally, an infra-red rejection filter can also be placed in the optical path between the dichroic mirror (4) and the camera (13).

The ratio of the focal length of the second image-combining optical unit (2) and the focal length of the optical unit (10) is determined to provide in the plane of the camera (1) an image whose smallest observed objects have a size of more than one pixel.

The equipment also includes a computer (12) receiving data from the camera (1) and a second camera (13) observing the target (11). This computer (12) also controls the scanner (9) and the laser (5).

The computer (12) runs computer programs to perform different processing tasks:
- the pre-processing of the raw images from the camera (1);
- a localization and characterization processing of the particles identified during the aforementioned pre-processing;
- a control processing of the scanner (9) and the laser (5) to match the laser's shots with the position of the particles; and
- optionally a processing of the raw images from the camera (13) observing the target (11).

The raw images from the camera are pre-processed. This pre-processing can be carried out periodically, to record a mapping of the film (3) before a laser triggering sequence is engaged, or between two consecutive triggering sequences.

The first solution is particularly suitable for situations where the film carries stable particles, both in terms of their location in the film plane and in terms of their development. This concerns, for example, mineral or organic particles that are not very reactive with respect to the substrate.

The second solution is better suited to situations where the particles are mobile and scalable. This is the case, for example, of living particles such as cells, which can move in the film with a strong tendency to aggregate that will strongly depend on the type of cell and medium used.

In both cases, the processing consists in extracting information from the raw images corresponding to the detection of graphic items corresponding to particles of interest, for example, by segmentation, shape recognition, or contour and center of gravity recognition techniques.

Watershed, Meyer's flooding algorithm or Optimal spanning forest algorithms thresholding techniques may be used to perform this mapping.

This processing can be divided into several phases:
- a phase of restoration or conditioning of the raw images (noise suppression, de-blurring, correction of non-uniform lighting);
- a segmentation phase;
- a characteristic extraction phase; and
- a data analysis phase.

This processing assigns to each identified graphic item an ID± identifier and a position in the form of Cartesian coordinates in the film plane.

Figure 2:
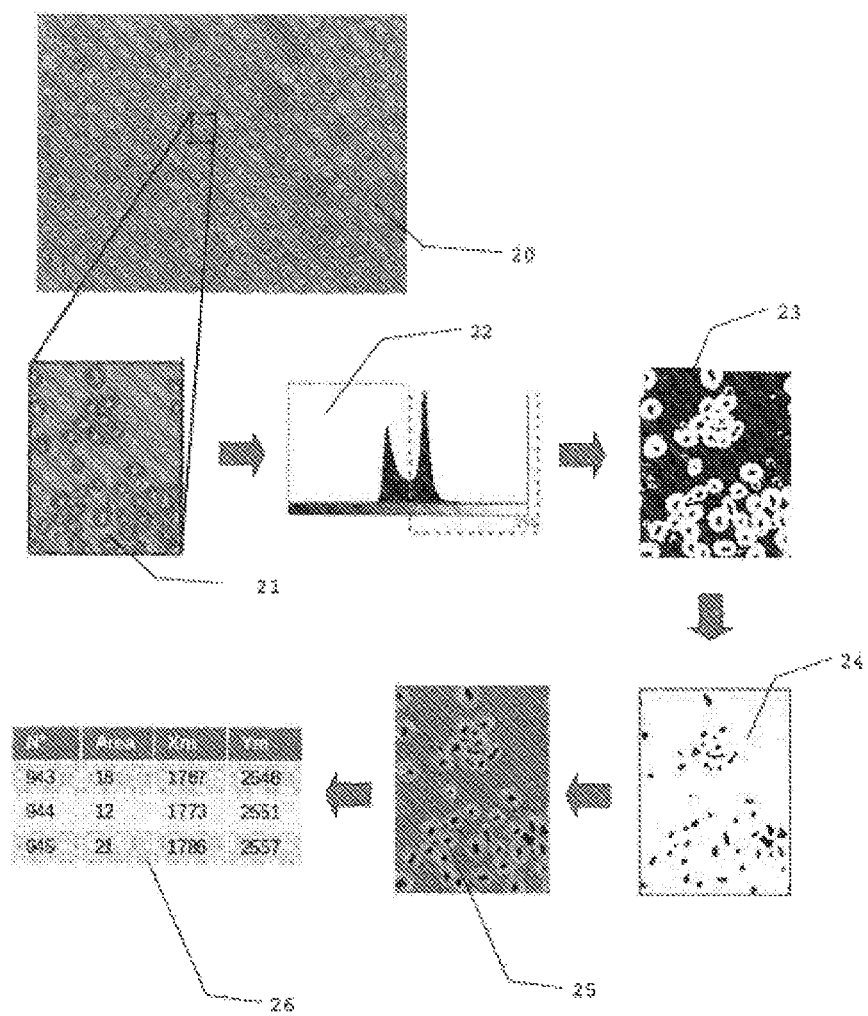
FIG. 2 shows views of the acquired images.

FIG. 2 shows the sequence of images, based on the raw image (20) captured by the camera (1), and an enlarged area (21) showing the presence of a plurality of particles in the image field.

A thresholding processing is used in a known manner to calculate a contrast variation in the form of a histogram, as shown in the image (22). This histogram allows calculation of a contrasted image (23) by using thresholding algorithms.

This contrasted image (23) is used to calculate the centroids (image (24)) and contours (image (25)).

This information makes it possible to build the table (26) of the identifiers of each processed graphic item and the coordinates of the center of each of these items.

The characterization processing consists in assigning attributes to each of the identified and localized graphic items according to their affiliation to a family predefined by these physical parameters such as:
- the size class of the item
- reaction to specific lighting, e.g., photoluminescence
- spectral characteristics
- the type of contour (shape, regularity, etc.)
- the affiliation to an aggregate of items
- the optical density of the item
- the density of the aggregate (estimated number of aggregated items)
- spatio-temporal dynamics These parameters are of course not limiting.

The result of this processing completes the above table by adding to each identifier information about the affiliation to one or more series of classes.

Processing is preferably made in parallel and run on parallel architecture processors, such as GPUs.

The information is then used to match the mapping thus carried out with the previously recorded target map in order to calculate a sequence of laser shots resulting in the calculation of a scanner orientation and then the triggering of the laser pulse, under the control of the computer (12). The calculation of the sequence takes into account a calculation of the reduction of the global process time, by known algorithms such as "resolution of the commercial traveler's optimization problem or of the NP-complete problem.".

After each laser shot or after a series of laser shots, the computer checks the conformity of the transfers by comparing the image transmitted by the camera (13) observing the target (11) and the pre-registered target map. The calculator performs a maximum likelihood calculation, and in case of a discrepancy (lack of printed items), recalculates the following sequence of laser shots to correct the observed anomalies. It can also be used to correct areas where there have been too many printed items with respect to the target map. This correction is generally done by conventional suction means that allow very precise removal of small quantities of material. This suction is controlled by the computer (12). In any case, control here means the installation of a control loop between the pre-recorded target map and the target (11) actually printed, which must make it possible to obtain a maximum likelihood as close as possible to 100% between both maps.

Moreover, the present disclosure is not limited to a single laser printing process. It covers multi-head printing (several films (3) used at the same time with one or more lasers), for which it is imperative that the imaging means and their associated processing be capable of processing several areas simultaneously in order to guarantee the possibility of simultaneous "multicolor" printing (several different cellular types printed in a single process).

The invention claimed is:

1. An apparatus for transferring bio-ink to a target, comprising:
   a slide defining a reception area for a fluid film containing heterogeneities;
   a laser associated with a controlled deflection device and an optical unit for focusing a laser beam emitted by the laser in a plane of the fluid film to apply a localized laser pulse, the slide being transparent to the laser beam;
   an imager located and configured to acquire an image of an imaging area of the fluid film, the imaging area being at least five times larger than a nominal cross-section of an inhomogeneity of the fluid film, the slide being transparent in the spectral domain of the imager;
   a computer configured to analyze the acquired image and recognize geometric positions of inhomogeneities in the fluid film and an observable characteristic of each of the recognized inhomogeneities; and
   wherein the apparatus is configured to select at least one of the recognized inhomogeneous zones, and control the deflection device to direct the laser beam toward the position of the inhomogeneous zone and trigger the localized laser pulse.

2. The apparatus of claim 1, wherein the inhomogeneities of the fluid film comprise particles.

3. The apparatus of claim 1, wherein the inhomogeneities of the fluid film comprise biomaterials.

4. The apparatus of claim 1, wherein the inhomogeneities of the fluid film comprise biochemical species.

5. The apparatus of claim 1, wherein the inhomogeneities of the fluid film comprise a combination of particles and/or biomaterials and/or biochemical species.

6. The apparatus of claim 1, wherein the imaging area is greater than one square millimeter.

7. The apparatus of claim 1, wherein the imaging area includes an area of interaction between the laser beam and the fluid film.

8. The apparatus of claim 1, wherein the imaging area is distinct from an interaction area between the laser beam and the fluid film.

9. The apparatus of claim 1, wherein the computer is remote from the laser, imager, and slide, the apparatus further comprising means of communication between the imager and the computer.

10. The apparatus of claim 1, further comprising a spectrometer.

11. The apparatus of claim 1, wherein the fluid film comprises living cells.

12. The apparatus of claim 1, wherein the apparatus is configured to form more than one area of interaction between laser beams and the fluid film.

13. The apparatus of claim 1, further comprising a suction system for removing excess printed material from a printing area.

14. The apparatus of claim 1, further comprising means for imaging a printed substrate.

15. The apparatus of claim 1, wherein the imager is configured to acquire images in real time.

16. A method for transferring bio-ink to a target, comprising:
- placing in a transfer equipment a transparent slide defining a reception area for a transparent fluid film containing a plurality of inhomogeneities;
- at least one imaging step of acquiring an image of an area of the film, the image having an image cross-section at least five times larger than a nominal cross-section of an inhomogeneity;
- at least one image analysis step of locating geometric positions of the inhomogeneities and characterizing at least one observable characteristic of each of the located inhomogeneities;
- at least one selection step of selecting one of the located and characterized inhomogeneities; and
- at least one transfer step comprising controlling an orientation and activation of a laser pulse emitted by a laser associated with a controlled deflection device and directing the laser beam to the position of one inhomogeneity and triggering a laser pulse and interaction of the laser beam with the film at the location of the one inhomogeneity.

17. The method of claim 16, wherein the inhomogeneities comprise particles.

18. The method of claim 16, wherein the inhomogeneities comprise biomaterials.

19. The method of claim 16, wherein the inhomogeneities comprise biochemical species.

20. The method of claim 16, wherein the inhomogeneities comprise a combination of particles, and/or biomaterials and/or chemical species.

21. The method of claim 16, wherein the at least one transfer step comprises a plurality of transfer steps each corresponding to at least one localized and characterized inhomogeneity.

22. The method of claim 16, wherein the at least one transfer step is performed after the at least one imaging step, the at least one image analysis step, and the at least one selection step.

23. The method of claim 16, further comprising a step of calculating an ordered sequence of inhomogeneities to be transferred.

24. The method of claim 16, wherein the at least one imaging step comprises processing an acquired image to extract simplified patterns corresponding to imaged inhomogeneities.

25. The method of claim 16, wherein the locating of the geometric positions of the inhomogeneities and the characterizing of the at least one observable characteristic of each of the inhomogeneities are carried out simultaneously.

26. The method of claim 16, wherein the locating of the geometric positions of the inhomogeneities and the characterizing of the at least one observable characteristic of each of the plurality of inhomogeneities are performed by processing by algorithms executed on processors with parallel architecture.

27. The method of claim 16, further comprising a step of comparing an acquired image of a transfer area after the at least one transfer step with a map of an intended implantation.

28. The method of claim 27, further comprising an additional step of triggering another at least one transfer step to correct a difference between the acquired image and the map of the intended implantation.

29. The method of claim 27, further comprising a suction step to correct a difference between the acquired image and the map of the intended implantation.

30. The method of claim 16, wherein the transparent fluid film comprises living cells.

* * * * *